(12) United States Patent
Bucki et al.

(10) Patent No.: US 8,724,926 B2
(45) Date of Patent: May 13, 2014

(54) METHOD FOR REGISTERING A SET OF POINTS IN IMAGES

(75) Inventors: Marek Bucki, La Tronche (FR); Yohan Payan, Allevard (FR)

(73) Assignees: Universite Joseph Fourier—Grenoble 1, St. Martin d'Heres (FR); Centre National de la Recherche Scientifique (CNRS), Paris (FR)

( * ) Notice: Subject to any disclaimer, the term of this patent is extended or adjusted under 35 U.S.C. 154(b) by 252 days.

(21) Appl. No.: 13/122,116

(22) PCT Filed: Oct. 2, 2009

(86) PCT No.: PCT/EP2009/062829
§ 371 (c)(1),
(2), (4) Date: Mar. 31, 2011

(87) PCT Pub. No.: WO2010/037852
PCT Pub. Date: Apr. 8, 2010

(65) Prior Publication Data
US 2011/0176746 A1 Jul. 21, 2011

(30) Foreign Application Priority Data
Oct. 3, 2008 (FR) ...................................... 08 56711

(51) Int. Cl.
*G06K 9/32* (2006.01)
*G06T 7/00* (2006.01)
(52) U.S. Cl.
USPC .......................................... 382/294; 382/293
(58) Field of Classification Search
CPC .................................................. G06T 7/0028
USPC ........................................................ 382/294
See application file for complete search history.

(56) References Cited

U.S. PATENT DOCUMENTS 7,072,705 B2 7/2006 Miga et al.
7,103,399 B2 9/2006 Miga et al.
(Continued)

FOREIGN PATENT DOCUMENTS

WO WO 2010/037852 4/2010

OTHER PUBLICATIONS

Leow et al., "Inverse Consistent Mapping in 3D Deformable Image Registration: Its Construction and Statistical Properties", IPMI 2005, LNCS 3565, pp. 493-503, 2005.*

(Continued)

*Primary Examiner* — Matthew Bella
*Assistant Examiner* — Jose M Torres
(74) *Attorney, Agent, or Firm* — Harness, Dickey & Pierce, P.L.C.

(57) ABSTRACT

The disclosure relates to an image processing method for estimating a brain shift in a patient, the method involving: the processing of a three-dimensional image of the brain of a patient, acquired before a surgical operation, in order to obtain a reference cerebral arterial tree structure of the patient; the processing of three-dimensional images of the brain of the patient, acquired during the operation, in order to at least partially reconstitute a current cerebral arterial tree structure of the patient; the determination from the combination of the reference and current cerebral arterial tree structures, of a field of shift of the vascular tree representing the shift of the current vascular tree in relation to the reference vascular tree; the application of the determined field of shift of the vascular tree to a biomechanical model of the brain of the patient in order to estimate the brain shift of the patient; and the generation, from the estimated brain shift, of at least one image of the brain of the patient, in which the brain shift is compensated.

9 Claims, 5 Drawing Sheets

(56) References Cited

U.S. PATENT DOCUMENTS

| | | |
|---|---|---|
| 7,647,087 B2 | 1/2010 | Miga et al. |
| 2006/0036167 A1 | 2/2006 | Shina |
| 2007/0021669 A1 | 1/2007 | Miga et al. |
| 2011/0176746 A1 | 7/2011 | Bucki et al. |

OTHER PUBLICATIONS

Miller, K. et al., "Mechanical Properties of Brain Tissue In-Vivo: Experiment and Computer Simulation"; Journal of Biomechanics 33 (2000); pp. 1369-1376.

Noblet, V. et al., "3-D Deformable Image Registration: A Topology Preservation Scheme Based on Hierarchical Deformation Models and Interval Analysis Optimization"; IEEE Transactions on Image Processing, vol. 14, No. 5, May 2005, pp. 553-566.

Penney, G.P. et al., "Registration of Freehand 3D Ultrasound and Magnetic Resonance Liver Images"; Medical Image Analysis 8 (2004) pp. 81-91.

Reinertsen, I. et al., "Validation of Vessel-Based Registration for Correction of Brain Shift"; Medical Image Analysis 11 (2007) pp. 374-388.

Skrinjar, O. et al., "Model-Driven Brain Shift Compensation"; Medical Image Analysis 6 (2002) pp. 361-373.

Slomka, P. et al., "Evaluation of Voxel-Based Registration of 3-D Power Doppler Ultrasound and 3-D Magnetic Resonance Angiographic Images of Carotid Arteries"; Ultrasound in Med. & Biol., vol. 27, No. 7, pp. 945-955, 2001.

Bucki, M. et al,"Framework and Bio-Mechanical Model for a Per-Operative Image-Guided Neuronavigation Including 'Brain-Shift' Compensation;" http://hal.archives-ouvertes.fr/docs/00/10/85/09/PDF/Brainshift_Santiago.pdf; Oct. 23, 2006.

Bucki, M. et al, "Framework for a Low-Cost Intra-Operative Image-Guided Neuronavigator Including Brain Shift Compensation;" Engineering in Medicine and Biology Society, 2007; Aug. 22, 2007, pp. 872-875.

Armspach, J. et al, "3-D Deformable Image Registration: A Topology Preservation Scheme Based on Hierarchical Deformation Models and Interval Analysis Optimization;" IEEE Transactions in Image Processing, vol. 14, No. 5, May 1, 2005; pp. 553-566.

Noblet, V. et al, "Retrospective Evaluation of a Topology Preserving Non-Rigid Registration Method," Medical Image Analysis, Oxford University Press, vol. 10, No. 3, Jun. 1, 2006, pp. 366-384.

Miller, M. et al, "Group Actions, Homeomorphisms, and Matching: A General Framework," International Journal of Computer Vision, vol. 41, No. 1-2; Feb. 2001; pp. 61-84.

* cited by examiner

FIG. 3
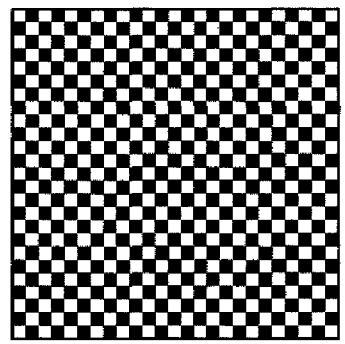
(a)
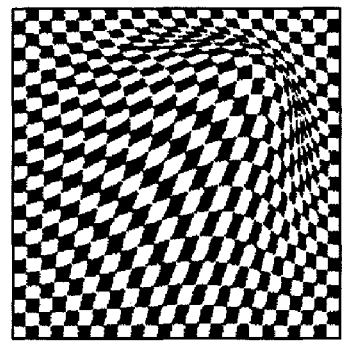
(b)
FIG. 4
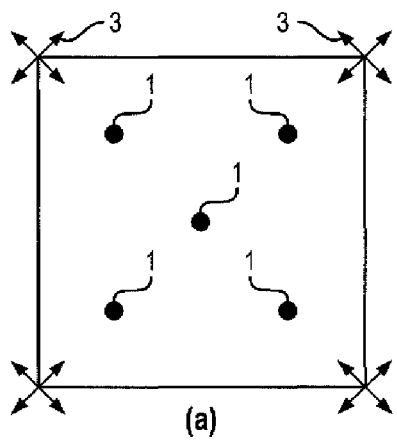
(a)
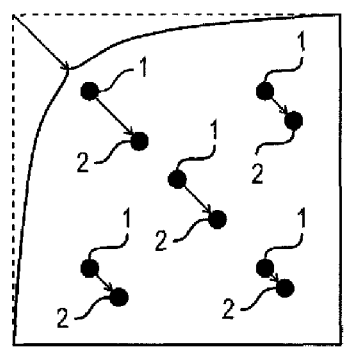
(b)
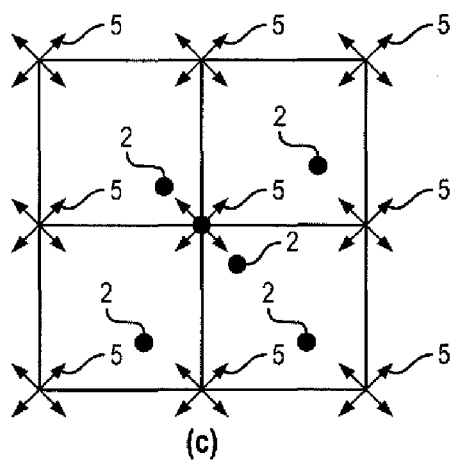
(c)
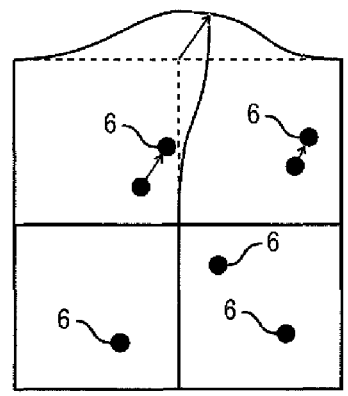
(d)

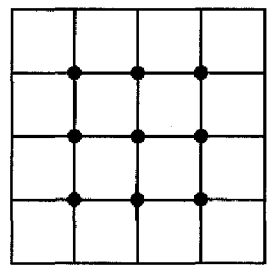
(a)
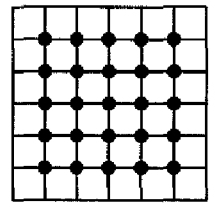
(b)
FIG. 5
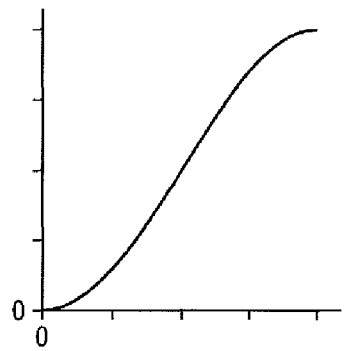
(a)
FIG. 6
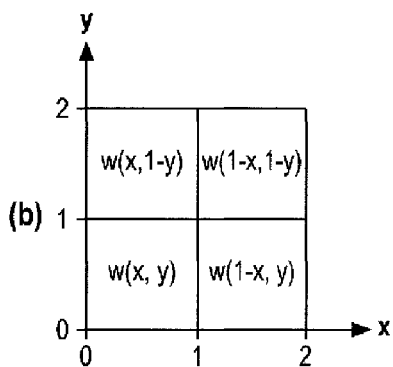
(b)
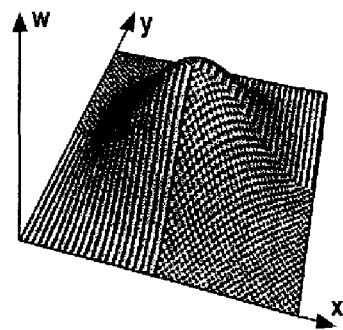
(c)

METHOD FOR REGISTERING A SET OF POINTS IN IMAGES

CROSS-REFERENCE TO RELATED APPLICATIONS

This application is a National Phase Entry of International Application No. PCT/EP2009/062829, filed on Oct. 2, 2009, which claims priority to French Patent Application Serial No. 0856711, filed on Oct. 3, 2008, both of which are incorporated by reference herein.

FIELD OF THE INVENTION

The present invention concerns the field of computer-assisted surgery, and more particularly a system and method allowing the registration of an organic tissue in two images.

BACKGROUND

The precise locating of a target is essential during surgical procedure to reduce the morbidity rate. During the course of a surgical procedure shift deformation of organic tissues may occur. For example, during surgical procedure for ablation of a brain tumour, this deformation may occur after an opening has been made in the patient's skull. Such deformation may be related to physical phenomena (gravity, loss of cerebrospinal fluid, neurosurgeon manoeuvres, etc.) or to physiological phenomena (tumefaction due to osmotic drugs, anaesthetics, etc.) of which some are currently unknown.

To compensate for this shifting of organic tissues and to retrieve the pre-operative data of the patient during the surgical procedure, shift compensation for organic tissue deformation can be achieved on the following principle. A first image of a region of the organic tissues is acquired before the surgical operation. During the surgical operation, a second image of the same region is acquired. System processing means process these two images to align the points in the two images to offset the shifting of organic tissues. To align the points in the two images, the processing means use an image registration method. However, registration methods do not allow the points in two images to be exactly aligned when the characteristics of the data given in the two images are heterogeneous.

It is one objective of the present invention to propose a method for registering a set of source points in a first image with a set of target points in a second image, the set of source points being of different type to the set of target points due to the difference between overlapping data regions or to the presence of noise.

SUMMARY

For this purpose, the invention provides a method for registering a set of source points S in a reference image, representing an organic tissue, with a set of target points D in a current image representing the deformed organic tissue, the method comprising the determination of a registration function R by iterative minimization of a registration energy $E_{reg}$, the registration function corresponding to a transformation allowing the mapping of source points S in the reference image to corresponding target points D in the current image, characterized in that the registration function R is an elastic registration function meeting the conditions required to guarantee heed of physical criteria of the organic tissue, the conditions comprising:

the Jacobian of the elastic registration function is higher than 0,
the registration function is continuously differentiable
the registration function is bijective.

Therefore the elastic registration function is determined so as to guarantee the heed of physical criteria associated with the organic tissue it is desired to register.

These physical criteria to be heeded are the following:
no folding-over of the organic tissue (which translates as the fact that the Jacobian of the registration function must be higher than 0),
regular propagation of organic tissue displacement (which translates as the fact that the registration function is continuously differentiable),
non-superimposition of two different points in the initial space at a single point in the deformed space, and the extent of the deformation function extended to the entire space (which translates as the fact that the function is bijective).

Preferred but non-limiting aspects of the present invention are the following:
the set of source points is of different type to the set of target points,
the registration energy $E_{reg}$ of the registration function (R) meets the following equation:

$$E_{reg} = \sum_{s \in S} d(R(s), D)$$

where: s is a point of the set of source points S,
R(s) is the transform of point s by the registration function R,
d(R(s),D) is the Euclidian distance between the transform of point s by the registration function and the set of target points denoted D;
the method comprises a direct filtering step wherein each point s of the set of source points S, whose association with a point d in the set of target points D verifies a rejection criterion, is deleted so as to obtain a filtered set of source points S',
the rejection criterion is that the distance between:
the transform of point s of the set of source points S by the registration function, and
the corresponding point d in the set of target points D is greater than a maximum predetermined value.

The method further comprises an inverse filtering step wherein each point d of the set of target points D, whose association with a point s of the set of source points S verifies another rejection criterion, is deleted so as to obtain a filtered set of destination points D',
the other rejection criterion is that the distance between:
the inverse transform of point d of the set of target points D by the inverse registration function, and
the corresponding point s' in the filtered set of source points S' is greater than the predetermined maximum value.

The invention also concerns a system for registering a set of source points in a reference image, representing an organic tissue, with a set of target points in a current image representing the deformed organic tissue, characterized in that it comprises means for implementing the above-described method. The invention also concerns a computer programme product comprising programme code instructions recorded on a medium which can be used on a computer, characterized in that it comprises instructions for implementing the above-described method.

BRIEF DESCRIPTION OF THE DRAWINGS

Other advantages and characteristics will become better apparent from the following description of several variants of embodiment given as non-limiting examples, with reference to the appended drawings in which:

FIG. 3 illustrates deformation of a unit square with folding of space;

FIG. 4 is a two-dimensional illustration of a multi-scale iterative approach described in connection with the organic tissue registration step;

FIG. 5 illustrates cells inserted in the margin of discretization for two successive refining levels;

FIG. 6 illustrates a form function w;

DETAILED DESCRIPTION

A more detailed description will now be given of one embodiment of the registration method according to the invention. This registration method will be presented within the setting of an image processing method to estimate brain shift. However, this registration method is evidently fully independent of the processing method to estimate brain shift.

More precisely, the registration method of the invention:
can be implemented for registering organic tissues other than the brain, and/or
can be implemented in other types of image processing methods.

General Principle of the Processing Method to Estimate Brain Shift

As explained in the foregoing, the precise locating of a surgical target is essential to reduce morbidity rate during surgical excision of a brain tumour. When the size of the craniotomy is extensive, deformation of brain soft tissue may occur during the procedure. On account of this brain shift, preoperative data no longer correspond to the reality, and neuro-navigation is highly jeopardized.

With the present invention, it is possible to take this shift into account and to compute a corrected position of the brain's anatomical structures in order to locate ancillaries. Before surgical procedure on a patient's brain, a magnetic resonance angiogram (MRA) of the brain can be acquired. During the procedure, further to major brain shift, the surgeon carries out Doppler ultrasound scanning of the region of interest.

The processing method to estimate brain shift allows preoperative data to be updated in relation to brain shift occurring during the procedure. To do so, it is proposed to track the deformation of a particular anatomic structure i.e. the cerebral vascular tree, throughout the procedure. Owing to its distribution within the volume of the parenchyma, displacements of the vascular tree are representative of global tissue deformation.

The arteries and arterioles irrigating neural tissues lie both in the deep parts of the encephalon but also on the surface, and more particularly in the vicinity of the tumour whose development entails angiogenesis and hence the formation of new vessels. By locating the vascular tree relative to its initial position at the start of the procedure, it is possible to infer displacements of the vessels thereof caused by brain shift. This information, far from being dense within the global volume, remains localized to certain regions.

It is therefore proposed to use biomechanical modelling of the patient's brain to extrapolate global deformation on the basis of the displacement of the cerebral vascular tree. The global displacement field thus obtained is then applied to all the preoperative data for updating thereof.

Description of One Embodiment of the Method for Estimating Brain Shift

Figure 1:
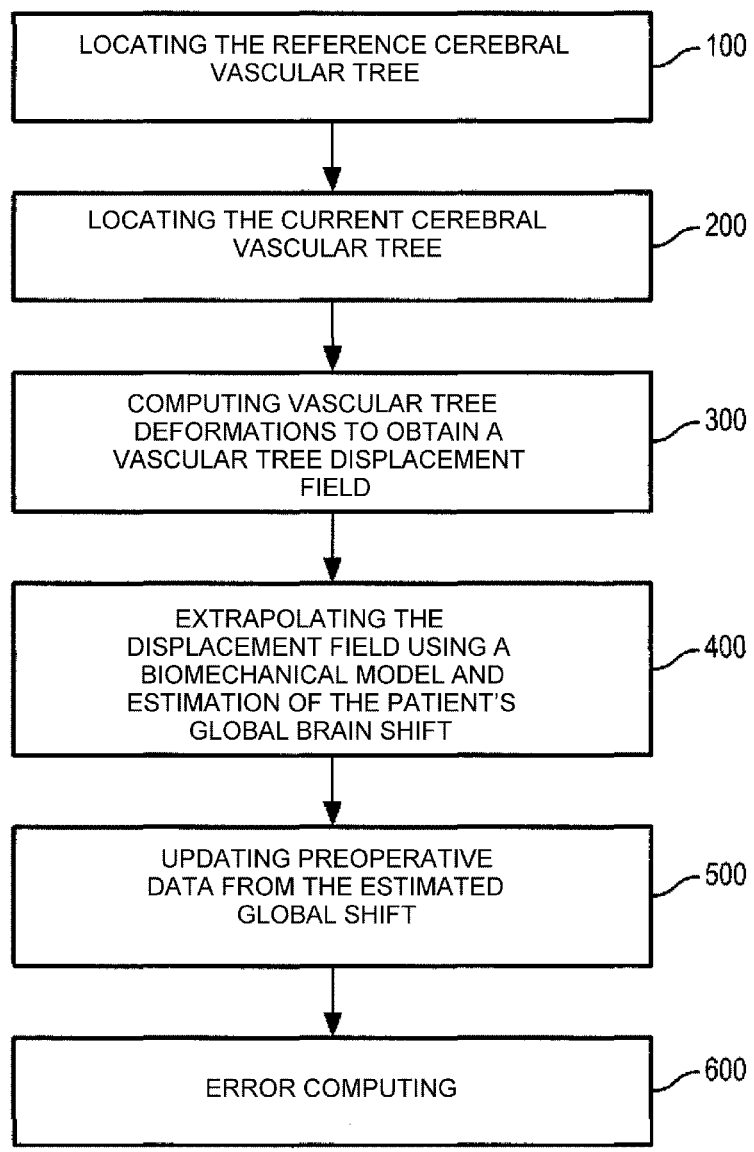
FIG. 1 illustrates one embodiment of the method of the invention.

With reference to FIG. 1, different steps of the method for estimating brain shift are illustrated. The image processing method for estimating brain shift comprises the following steps:

processing 100 a three-dimensional image of the patient's brain acquired before surgical procedure, to obtain a reference cerebral arterial tree of the patient, processing 200 two-dimensional images of the patient's brain acquired during the operation, for at least partial reconstitution of a current cerebral arterial tree of the patient, determining 300, from matching of the reference and current cerebral arterial trees, a deformation field of the vascular tree representing the displacement of the current vascular tree relative to the reference vascular tress, applying 400 the determined deformation field of the vascular tree to a biomechanical model of the patient's brain to estimate the global shift of the patient's brain; this model is used as mechanical interpolator to calculate all volume displacements inside the brain throughout the procedure, generating 500, from the estimated brain shift, at least one image of the patient's brain in which there is compensation for the brain shift.

Determining the Reference Cerebral Vascular Tree

As described in the foregoing, the method comprises a step 100 to process an image of the patient's brain acquired before the surgical procedure. The purpose of this processing is to locate the cerebral vascular tree in the image acquired before the surgical procedure. This cerebral vascular tree in the image, acquired before the surgical procedure corresponds to the vascular tree before shifting of the patient's brain, and will be called hereunder the "reference cerebral vascular tree".

Preferably, the image acquired before the surgical procedure is a three-dimensional image. Further preferably, this three-dimensional image is a magnetic resonance angiogram. Magnetic resonance angiography can reveal major contrast between tissues. Analysis of the magnetic resonance angiogram allows a precise distinction to be made between the types of tissues observed.

In particular the data it contains allows locating of the reference cerebral vascular tree. Also, the technique allowing the acquisition of a magnetic resonance angiogram has the advantage of being non-invasive and hence without danger for the patient, contrary to techniques which emit ionizing radiation for example such as tomography.

Once the patient is placed on the operating table, the processing of the three-dimensional image to obtain the reference cerebral arterial tree comprises a step to orientate the three-dimensional image relative to the patient's head. In other words, the spatial position of the reference vascular tree is determined relative to a reference frame of the patient's physical space. More precisely, the reference cerebral vascular tree is transposed to the patient's physical reference frame by means of a so-called rigid registration technique which is based on matching calibration points with their segmented equivalents in the magnetic resonance angiogram acquired before the operation.

Under the present invention by "rigid registration" is meant a geometric transformation consisting of a rotation and a translation. Computing can then be used to find the transformation between the two systems of coordinates.

The calibration points used may be points or salient anatomic surfaces such as the tip of the nose, supraorbital ridge, the surface of the cheeks or forehead. The calibration points may also be defined by a plurality of adhesive discs (at least three and preferably ten) positioned on the patient's skin before acquisition of the magnetic resonance angiogram. These discs are therefore acquired in the angiogram at the same time as the patient's brain.

The radiometric equivalents of the calibration points can be identified in the magnetic resonance angiogram. Once the patient is installed on the operating table, the surgeon indicates the position of each calibration point to a locating system by means of a probe. The locating system may be an optical locating system (for example comprising a stereoscopic camera) or a magnetic locating system or any other locating system known to persons skilled in the art.

Knowing the position of the reference cerebral vascular tree relative to the calibration points, and knowing the position of the calibration points once the patient is installed on the operating table, the system is capable of calculating the spatial position of the reference vascular tree relative to the spatial position of the patient. Registration between the images and the patient performed at the start of procedure allows the subsequent locating in the operative field of all the elements identified in the magnetic resonance image, and reciprocally to transpose the position of the ancillaries onto the volume of data in order to monitor and control the proper conducting of the surgical procedure.

Determination of the Current Cerebral Vascular Tree

The method further comprises a step 200 which comprises processing a plurality of two-dimensional images of the patient's brain, acquired during the operation, for at least partial reconstitution of a cerebral arterial tree called the patient's "current cerebral arterial tree". Throughout the surgical procedure, further to major brain shift of the patient, the surgeon acquires two-dimensional images.

Under the invention by "plurality of two-dimensional images" is meant 2D images within a determined (3D) volume, whose acquisition planes are secant or parallel. These 2D images can be obtained using any medical 2D or 3D image acquisition device such as 3D ultrasound images for example. Preferably, these two-dimensional images are ultrasound images acquired in Doppler mode, using a probe located by the locating system.

The ultrasound images in Doppler mode allow visualization of blood flows. Also the Doppler ultrasound technique has the advantage of being innocuous for the patient. Intra-operative Doppler ultrasound is therefore a good instrument for investigating brain shift during the procedure. This visualization mode is based on Doppler Effect and, by analyzing variations in the frequency of emitted ultrasound, allows tissue displacements to be located such as blood flows. The segmenting of these types of images is made easier on account of the colour coding used to represent flow velocities. With this modality it is therefore possible to visualize blood flows along the vascular tree within the volume of the encephalon, and thus to identify the position of the vessels which irrigate the parenchyma.

The acquisition of two-dimensional images is achieved as follows for example. The located probe is contacted with the patient's brain through the craniotomy made by the surgeon. A rotational movement is manually imparted to the located probe so that the ultrasound plane scans the largest possible part of the brain around the tumour.

The located probe comprises a marker enabling the locating system to define its position and orientation relative to the patient's physical reference frame, and hence to reposition the two-dimensional images spatially within the patient's physical reference frame. After the acquisition of a series of two-dimensional images, these are processed to locate the patient's current cerebral vascular tree. More precisely, the centres of the vessels contained in each two-dimensional image are selected so as to obtain a point cloud. This point cloud at least partly represents the patient's current cerebral vascular tree.

Registering the Reference and Current Vascular Trees

At another step 300 of the method, the reference and current vascular tree are matched to determine a deformation field representing the displacement of the current vascular tree relative to the reference vascular tree. More specifically, the reference vascular tree is registered with the current vascular tree.

By "elastic registration" is meant the determination, from datasets which represent two digital images of one same region, of a transformation allowing mapping between the reference image and current image. In other words, it entails "best" overlaying of the structures contained in two comparable images. The data derived from the three-dimensional image and from the two-dimensional images are of different type.

On one hand, the reference vascular tree obtained from pre-operative data is practically continuous, the entire patient's head is contained within the volume of data, and segmenting does not so to speak generate any artefacts in the reconstruction of the cerebral vascular tree. On the other hand, the current vascular tree obtained from intra-operative two-dimensional images is composed of a point cloud, and these two-dimensional images only cover a fraction of the volume of the brain. Depending upon the skill of the operator, the two-dimensional images may be more or less regularly distributed in space, some regions comprising multiple acquisitions whilst others do not contain any acquisition.

The task incumbent at registration step 300 of the cerebral vascular trees is therefore to estimate an elastic transformation between:
- the current intra-operative configuration of the vascular tree defined by a scattered, redundant, incomplete and noisy point cloud, and
- the reference configuration defined by complete noise-free data obtained from pre-operative imaging.

The deformation field is then computed from the correspondence determined between the reference vascular tree and the current vascular tree. The origin of each vector of the deformation field is a point of the reference vascular tree and designates a deformed point of the current vascular tree.

Elastic registration is guided by minimizing registration energy. This registration energy quantifies the similarity between the current vascular tree and the reference vascular tree. Optimal registration is achieved with zero registration energy. The objective of the elastic registration step is iteratively to minimize the value of this registration energy by causing the points of the current vascular tree to move towards the points of the reference vascular tree.

The rapidity of computing is obtained by means of:

prior computing of a distance map—between each point of the current vascular tree and its counterpart in the radiometric sense (i.e. the point which designates the same structure) in the reference vascular tree—on which evaluation of the registration energy is based, and determining the direction of the steepest descent computed on each iteration of the minimization process.

Given the scattered and irregular nature of the data, the search for an elastic registration function must be constrained so as not to arrive at an aberrant registration. The elastic registration function is a non-linear transformation allowing mapping from the current vascular tree to the reference vascular tree. More precisely, the conditions related to the type of data it is desired to register are determined to guarantee heed of essential physical criteria.

Since the data concerns organic data, one first condition which must be met by the elastic registration function is non-folding of space. Shifting of the patient's brain cannot induce folding-over of the patient's brain.

A second condition which must be met by the elastic registration function concerns the continuity of deformation propagation. The reference and current vascular trees are observations of the physical phenomenon of brain shift. Similar to the process of brain shift in the patient, without tearing or resection of tissue, the registration function must be continuous and even continuously differentiable i.e. differentiable at every point of the domain and not having any differential discontinuity.

A third condition which must be met by the registration function is that two different points of the current vascular tree cannot have the same image in the reference vascular tree, and vice versa. The elastic registration function such as proposed in the invention has the advantage of being invertible with the desired degree of accuracy. Once this registration function has been computed, post-processing of the result produced by registration allows the elimination of aberrations due to the presence of noise in the data of the intra-operative two- or three-dimensional images.

All the displacements of the vascular tree that are finally selected form a deformation field representing displacement of the current vascular tree relative to the reference vascular tree. The reader will appreciate that the registration step can be applied to the registration of structures other than a cerebral vascular tree. In particular, the elastic registration presented above can be applied to the registration of any type of organic tissue.

Extrapolation of the Deformation Field of the Cerebral Vascular Tree to the Entire Volume of the Organ via a Biomechanical Model At another step 500 of the method, the determined deformation field of the vascular tree is applied to a biomechanical model of the soft tissues of the patient's brain to estimate the global shift of the patient's brain. This mathematical model formalizes a priori knowledge of the behaviour of the organ, and allows the global behaviour thereof to be inferred under local deformation constraints deduced from intra-operative observation, called boundary conditions.

The biomechanical model (also known as deformable model) plays a twofold role. First, the biomechanical model allows extrapolation of displacements of the vascular tree to the entire volume of the brain to simulate the effect of brain shift.

Second, the biomechanical model allows data adjustment. The estimation of the deformation field of the vascular tree is flawed with errors due to the imaging mode used, to the limitations of segmenting algorithms and to those of elastic registration computing in order to match the current vascular tree with the reference vascular tree. With the biomechanical model it is possible to harmonize the deformation field by deleting errors in the input data to the biomechanical model. This renders the method resistant to artefacts present in noisy data collected during the surgical procedure (i.e. the two- or three-dimensional ultrasound images).

The originality of the method therefore lies in the complementarity between a biomechanical model approximating the patient's cerebral tissue behaviour and tracking of a potentially noisy anatomical structure but representing brain shift by means of the cerebral vascular tree. On completion of step 500 of the method, the patient's global brain shift is estimated. A last step 600 of the method, and using the estimated global brain shift, concerns the generation of at least one image of the patient's brain in which there is compensation for brain shift. For example, this image is the three-dimensional image (or two-dimensional cross-sectional images of this three-dimensional image) acquired before the operation to which the patient's global estimated brain shift is applied so as to update pre-operative data in relation to the patient's estimated global brain shift.

Verification of the Coherency of Computed Deformation

Advantageously, the method may comprise a step to compute discrepancies between points in the generated image of the brain and one or more control two-dimensional images acquired during the operation. This enables the user to verify the coherency and accuracy of the computing performed by the above-described method. For this purpose, the user may for example acquire one or more control two-dimensional images of the patient's brain to compute the positioning error between the points of the control two-dimensional images and their counterparts in the image generated from the patient's estimated global brain shift.

For example, the user may scan the cerebral tissues in the region of interest whilst projecting the position of the vascular tree deformed by the model onto the control two-dimensional images. The overlaying of the two data items i.e. real-time Doppler obtained by scanning the organ, and simulated Doppler signal computed from the incidence of the located ultrasound slices relative to the vascular tree deformed by the system, enables the user to evaluate coinciding between the model and patient reality. The assessment of deformation quality allows the user to take a decision on whether or not to follow the indications of the system on the basis of the updated pre-operative data.

Since brain shift is a changing process, this validation is made immediately after the acquisition of the data on which the deformation algorithm is based, to guarantee the pertinence thereof. The above-described method is fully adapted to continuous monitoring of brain soft tissue deformation, both through its response times which are of the order of a few seconds, and through the repeatability of the data acquisition procedure which does not require any major interruption during surgical procedure or the providing of cumbersome equipment.

Theory Associated with Elastic Registration

A more detailed description will now be given of the theory associated with the elastic registration step. The explanations below are given in connection with the elastic registration of the cerebral vascular tree, but evidently this registration can be applied to other types of organic tissues.

Elastic registration is an application $R: \mathbb{R}^3 \to \mathbb{R}^3$, which minimizes a certain error of registration, or rather more a registration energy defined between a set of source points S and another set of target points D. Registration energy R is the measurement of a "similarity" between the set of transformed points R(S) and the target set (D). When the two sets merge then this energy becomes zero and registration is achieved. If the registration energy and the function space in which the transformation R takes place are not correctly defined, then the problem of finding an optimal R is ill-defined i.e. the existence and unity of R are not guaranteed.

In this part we will describe the framework for computing elastic deformation which allows robust establishment of elastic correspondence between the data under consideration. The specificities of this approach lie in the mathematical properties of transformation R, shown further on, which guarantee the physical realism thereof.

Registration Energy

Registration energy can be freely defined to reflect the type of registration problem concerned. For example for registration between two images, this measurement can be based on the differences between the pixel or voxel values of the source and target images. In the case in hand, the similarity between the datasets S and D is defined by the spatial proximity of the two point clouds. Without any other knowledge of the type of data being handled, it is possible for example to define registration energy $E_{reg}$ as the mean of the minimum Euclidian distances between R(S) and D.

$$E_{reg}(R) = \frac{1}{\text{Card}(S)} \sum_{s \in S} d(R(s), D) + \frac{1}{\text{Card}(D)} \sum_{d \in D} d(d, R(S))$$

where: R represents the elastic registration function,
  Card(S) is the cardinal of the source set S,
  Card(D) is the cardinal of the target set D,
  d(R(s),D) represents the distance between set D and the transform by R of a point s in set S,
  d(d,R(S)) represents the distance between a point d of set D and the transform by R of set S.

In this case, optimal registration is achieved when the value of $E_{reg}$ cancels itself out. The symmetric energy presented above assumes that each structure present in S can, by means of a suitable transformation R, find a match among D, and reciprocally. The designations "S" and "D" of the two datasets are interchangeable.

In the case in hand however, the structures present in S and D may not be equivalent and the assumption of symmetry does not hold since the structures in S only represent a sub-set of D. An alternative definition must be found to take this into consideration. Henceforth, "S" shall designate all the points defining the current, intra-operative configuration of the vascular tree, and D shall designate those which define the pre-operative reference configuration thereof. The elastic registration function R is therefore the function which maps the points of S to D, and an asymmetric definition of the energy of this registration can be formulated by truncating the above symmetric expression:

$$E_{reg}(R) = \frac{1}{\text{Card}(S)} \sum_{s \in S} d(R(s), D)$$

The meaning of the names "source" and "target" can be better grasped by viewing elastic registration as an iterative process in which the source points S are moved towards the target set along an optimal trajectory on a surface of potential energy whose relief is defined by the spatial configuration of the points in D. The evaluation of a candidate configuration R(S) is made on the set containing fewer data, whilst the energy function is more strictly defined by D which contains the reference information on the entire structure of the vascular tree. Alternative solutions to the problem of asymmetry can be found in the literature. The above definition of $E_{reg}$ can lead to situations in which a group of source points is registered to a confined part of D, in other words this energy does not promote distribution of the point sources over the target structure. To avoid this situation, it is possible to extend its expression by adding a term which quantifies this distribution but which operates solely in a restricted neighbourhood of D points which contain R(S) points.

Finally, since the cardinal of set S does not change throughout registration, it is also possible to simplify the preceding expression of energy $E_{reg}$ by eliminating its preceding multiplicative constant, which leads us to the following definition of $E_{reg}$:

$$E_{reg}(R) = \sum_{s \in S} d(R(s), D)$$

Space of Deformation Functions

Given the scattered, irregular nature of the data, the search for an elastic registration function must be constrained so as not to arrive at an aberrant registration. This pitfall is chiefly due to numerous local minima scattered over the product of the energy function for a given D configuration. The two sets S and D are observations of the physical phenomenon being examined i.e. brain shift.

It is therefore assumed that in similar manner to the brain shift process, without any tearing or resection of tissue, the non-linear transformation R being sought is continuous and even continuously differentiable i.e. differentiable at every point of the domain and does not exhibit any differential discontinuity. This defines a first restriction on the search space of the registration functions: $R \in C^1(\mathbb{R}^3)$.

A further strong constraint on the nature of the transformation is that it must not entail folding of space. The non-folding constraint can be mathematically expressed as follows. Let us consider a trihedron oriented positively consisting of three infinitesimal vectors $dX_1$, $dX_2$ and $dX_3$ placed at a point p of the space. Let dV denote the positive volume defined by these three vectors and whose value is given by the determinant of the matrix formed by the three vectors.

$$dV = (dX_1 \times dX_2) \cdot dX_3 = |dX_1 dX_2 dX_3|$$

After application of R transformation at point p, the three vectors are transformed to dx1, dx2 and dx3. The infinitesimal nature of these vectors allows the following approximation:

$$\forall i = 1, 2, 3, \, dx_i = \frac{\partial R}{\partial p}(p) dX_i$$

The volume defined by the transformed trihedron, denoted dv, is then obtained in similar manner:

$$dv = |\, dx_1 \quad dx_2 \quad dx_3 \,| = \left| \frac{\partial R}{\partial p}(p) \right| |\, dX_1 \quad dX_2 \quad dX_3 \,| = |J_R(p)| dV$$

The non-folding constraint is then quite simply written: $dv>0$. This means that the deformed infinitesimal volume has not been "folded over" ($dv<0$) by R or fully crushed ($dv=0$). Therefore the application of R does not locally fold over space if and only if its Jacobian at p is strictly positive. In our case, elastic registration must not fold space at any point, which leads to the expression of the non-folding constraint:

$$\forall p \in \mathbb{R}^3, |J_R(p)|>0$$

If, at a given point, the Jacobian is greater than 1, this means that the elastic registration locally stretches the volume; if, on the contrary, it is smaller than 1, then the volume is contracted. Finally, the product of the Jacobian matrix of R computed at a point by a unit vector gives us the stretching or contraction rate of the space in a given direction in the neighbourhood of this point. FIG. 3 shows the deformation of a unit square with folding of space.

Finally, for the same physical reasons, the application R must be injective. This translates as the fact that two separate points cannot have the same image by R, and physically R must not bring two atoms to one same point in space. If R is an injection, then for each point reached $p \in \text{Image}(R)$, a predecessor can be computed.

In the case in hand in which S represents a fraction of the structure present in D, the transformation that is sought in fine is the one which brings D to S, i.e. $R^{-1}$, in order to map the deformation field of the vascular tree in the reference configuration D to the current configuration S as described above. For the expression $R^{-1}$ to have a meaning, we need $D \subset \text{Image}(R)$. To simplify these considerations, it is considered that the R functions are surjective i.e. such that $\text{Image}(R) = \mathbb{R}^3$ it is therefore possible to conclude that the registration function R that is being sought is bijective.

The non-folding constraint guarantees that the Jacobian is strictly positive at every point of $\mathbb{R}^3$, yet this is insufficient to guarantee global bijectivity. The function space must therefore be suitably defined to ensure the bijectivity of function R. The following sections describe the registration strategy adopted to arrive at minimization of registration energy whilst paying heed to the above-mentioned constraints of differentiability, non-folding and bijection.

Computing of Registration

The approach presented here is inspired by mechanical modelling of solids based on discretization of finite-element type. To approximate the mechanical behaviour of non-structured data, it is assumed that the point cloud subjected to deformation is encompassed in a virtual elastic solid. Since displacement of the points translates the physical properties of an underlying structure whose geometry is unknown, the shape of a box surrounding the points is arbitrarily given to this virtual solid. All admissible deformations are then defined as the successive combinations of elementary deformations of the encompassing solid, whose effects are propagated throughout its volume and modify the position of the inner points. The elementary deformations mentioned here are defined later on. This described 3D registration technique can easily become a 2D registration technique by replacing the notion of "virtual solid" by "virtual plane". The illustrations presented below are based on a 2D implantation of registration for clarification of the concepts thereof.

The elastic registration function is assembled iteratively so that the registration energy $E_{reg}$ is optimally reduced with each step. Let $S_0 := S$ denote the initial cloud of source points, and let $S_i$ be the cloud of source points obtained after the iteration i. The domain of the virtual solid is discretized with a certain level of refining into regular hexahedrons (or squares, in 2D) called "cells". The elementary deformations of the solid are obtained by individually displacing the nodes of the mesh thus formed.

The uniting of the cells surrounding a node n defines its "neighbourhood" denoted V(n). An elementary registration function r is defined by propagating the displacement of the node n to all the points of $\mathbb{R}^3$ under the following constraints:

$$\begin{cases} \text{The boundary of the neighbourhood of } n, \partial V(n) \text{ remains} \\ \text{unchanged i.e.} \forall\, p \in \partial V(n), r(p) = p; \\ \text{The neighbourhood of } n \text{ remains globally unchanged i.e.} \\ r(V(n)) = V(n); \\ \text{All points lying outside this neighbourhood remain} \\ \text{unchanged i.e. } \forall\, p \notin V(n), r(p) = p. \end{cases}$$

Each node of the discretized solid is given consideration and the gradient of the registration energy, as a function of displacement of the node, is computed. The opposite of this vector defines the preferred displacement of this node i.e. the displacement which, when applied to the node, leads to the greatest reduction in registration energy.

Of all the nodes, the node which allows the greatest reduction in gradient is chosen and its preferred displacement is applied to it whilst the other nodes remain immobile. Local deformation of the solid is computed by propagating the displacement of the node through its neighbourhood, and the position of the source points it contains is modified accordingly, thereby giving the new configuration of the point cloud $S_{i+1}$.

Once the elementary deformation has been applied, the solid returns to its initial configuration, at rest, and the source points $S_{i+1}$ are distributed within its volume. A new iteration can then be computed using the new configuration $S_{i+1}$ as starting point. The iterations finally come to an end when no significant reduction in energy can be obtained by displacing the nodes of the mesh of the solid.

The above-described iterative loop assumes a degree of refining of the fixed domain $\Omega$. To maintain the spatial consistency of S throughout the assembling of R and to avoid fragmenting thereof, a multi-scale approach was adopted. The iterative assembling of R starts at the coarsest refining level and when the registration energy cannot be further improved at a given level, the cells are subdivided into 8 sub-cells (or 4, in 2D) similar to an octree.

The refining iterations come to an end when the manually specified maximum degree of subdivision has been reached. The size of the smallest cell reached during the refining process defines the dimensions of the smallest structure present in S and which will not be properly registered if an equivalent structure is missing in D.

FIG. 4 is a 2D illustration of the multi-scale iterative approach described above. The source points S are represented by the points referenced 1. Set D is not illustrated for better clarity. In (a) the initial set $S_0 := S$ is placed inside the virtual solid (referenced 2) discretized by a cell (level 1) and the gradients of the registration energy are computed at its four nodes 3. In (b) the best nodal displacement is applied to the solid and the source points are displaced in S1 (referenced 4). The solid then returns to its initial configuration (a). After several iterations, if no significant improvement in energy can be obtained, the refining level of the mesh is increased (c). The energy gradients are computed at the nine nodes 5 of the new mesh. In (d) the best displacement is applied to the solid and the new configuration of source points S2 (referenced 6) is computed.

By means of the "zeroing" technique of deformation of the solid after each iteration, large deformations of S can be envisaged without having to maintain an irregular mesh subjected to a sum of major deformations which would have been the case if the solid strictly followed the deformations of S. The regularity of the mesh before each iteration also allows substantial savings in computing efforts since the interpolation of nodal displacements can be computed on the basis of a cell of cubic type.

Before giving further details on the computing of R, we must extend the intuitive concept of the virtual solid so that each elementary deformation is defined as an application $\mathbb{R}^3 \to \mathbb{R}^3$ in order to meet the above-mentioned restriction. To do so, let us consider a source point placed on the boundary of the virtual solid $\partial\Omega$ for example close to the upper edge of the square in FIG. 4. If the node is displaced as is illustrated in (d) this point will fall outside the solid in its rest configuration (square) and will become a "dead point" whose position cannot be modified by the following iterations, which only have an effect on the cells of $\Omega$.

To overcome this disadvantage, a margin of cells is added around the domain, of identical dimensions to the dimensions used for discretization. This addition is made at each refining level. The outside nodes of these cells are fixed and therefore ensure an interface role between the deformable region and the remainder of $R^3$ which remains unchanged. FIG. 5 shows the additional cells 7 inserted in the margin of discretization of the domain with two successive refining levels.

Properties of Elastic Registration

Let G1, ..., GJ be the successive refining levels, G1 being the coarsest level and GJ the finest. Let $\{T_j^i: \mathbb{R}^3 \to \mathbb{R}^3, i \in [[1, I_j]]\}$ denote all the elementary deformations computed at each refining level j (where Ij is the total number of elementary deformations at level j). The expression of the elastic registration function R assembled iteratively is:

$$R: p \mapsto \left(\underbrace{r_J^{I_J} \circ \ldots \circ r_J^1}_{G_J} \circ \ldots \circ \underbrace{r_1^{I_1} \circ \ldots \circ r_1^1}_{G_1}\right)(p)$$

It is evident that the properties of differentiability, non-folding and bijection of R depend on the properties of the elementary registration functions r. If each $r_j^i$ is a bijection lir $R^3 \to R^3$ then the registration function R is also a bijection and its inverse is given by:

$$R^{-1}: p \mapsto \left(\underbrace{r_1^{1\,-1} \circ \ldots \circ r_1^{I_1\,-1}}_{G_1} \circ \ldots \circ \underbrace{r_J^{1\,-1} \circ \ldots \circ r_J^{I_J\,-1}}_{G_J}\right)(p)$$

If each $r_j^i$ is a continuously differentiable application $\mathbb{R}^3 \to \mathbb{R}^3$ then so is the registration function R. Let $p_0 \in \mathbb{R}^3$ be any point and pk the transformed point after application of k elementary deformations. Let K=I1+I2+ ... +IJ, then $\{p_k, k \in [[1, K]]\}$ is the whole of all the successive positions of p0 and R(p)=pK. The differential of R at p0 is given by the following composition rule:

$$J_R(p_0) = \frac{\partial R}{\partial p}(p_0) = \frac{\partial r_J^{I_J}}{\partial p}(p_{K-1}) \ldots \frac{\partial r_1^2}{\partial p}(p_1) \frac{\partial r_1^1}{\partial p}(p_0)$$

Finally, if all the $r_j^i$ verify the non-folding condition, then this is also true for the application R. This is the consequence of the expression of the Jacobian of R:

$$|J_R| = \left|\frac{\partial R}{\partial p}\right| = \prod_{j=1 \ldots J} \prod_{i=1 \ldots I_j} \left|\frac{\partial r_j^i}{\partial p}\right| = \prod_{j=1 \ldots J} \prod_{i=1 \ldots I_j} |J_{r_j^i}|$$

Therefore, to prove that any function R of the family of elastic registration functions generated by means of the above-described procedure verifies the constraints of differentiability, bijection and non-folding, it suffices to prove that these properties are indeed verified for each of the elementary registration functions $r_j^i$ which make up R.

Study of the Elementary Registration Functions

General expression of $r_j^i$

At this point, the family of elementary registration functions must be specified. In the Finite-element method, a node value (displacement or other quantity) is interpolated through the volume discretized by means of form functions $w: \mathbb{R}^3 \to [0, 1]$. The value of the form function associated with a node and evaluated at a point of the domain gives the proportion of the node value transferred to this point. Therefore the value of w at its node is 1. The same mechanism to propagate the displacement of a node through its neighbourhood will be used.

Consideration is given to the $i^{th}$ iteration of registration performed at refining level j and using the elementary registration function $r_j^i$. The indices of order and refining level i and j will be omitted in the remainder of this paragraph. Let $\vec{u}$ denote displacement and W the form function associated with the node which is displaced during this iteration. The expression of r is therefore:

$$r: \mathbb{R}^3 \to \mathbb{R}^3, p \mapsto p + w(p)\vec{u}$$

The conditions on the region of influence of r translate as constraints on the support of w as follows:

$$\begin{cases} \forall p \in \partial V(n), r(p) = p \Rightarrow w(p) = 0 \\ \forall p \notin V(n), r(p) = p \Rightarrow w(p) = 0 \end{cases}$$

It is noted that the support of w is supp(w)=V(n) which is a compact $\mathbb{R}^3$;

Differentiability

The differentiability of r derives from that of w. If $w: \mathbb{R}^3 \to [0, 1] \in C^1(\mathbb{R}^3)$, then $r \in C^1(\mathbb{R}^3)$ and the Jacobian matrix of r is written:

$$\frac{\partial r}{\partial p} =$$

$$Id_{3\times 3}+\begin{pmatrix}u_x\\u_y\\u_z\end{pmatrix}\begin{pmatrix}\frac{\partial w}{\partial x}&\frac{\partial w}{\partial y}&\frac{\partial w}{\partial z}\end{pmatrix}=\begin{pmatrix}1+u_x\frac{\partial w}{\partial x}&u_x\frac{\partial w}{\partial y}&u_x\frac{\partial w}{\partial z}\\u_y\frac{\partial w}{\partial x}&1+u_y\frac{\partial w}{\partial y}&u_y\frac{\partial w}{\partial x}\\u_z\frac{\partial w}{\partial x}&u_z\frac{\partial w}{\partial y}&1+u_z\frac{\partial w}{\partial z}\end{pmatrix}$$

where $Id_{3\times 3}$ is the identity matrix 3×3.

Therefore for r to be $C^1(\mathbb{R}^3)$ it is sufficient that w is also $C^1(\mathbb{R}^3)$.

Non-Folding

On rewriting the non-folding constraint using the expression of the Jacobian matrix of r, and by developing the determinant of the matrix, a new expression of the non-folding constraint is obtained:

$$\forall p\in\mathbb{R}^3, 1+\vec{\nabla}w(p)\cdot\vec{u}>0$$

Since $p\to\|\vec{\nabla}w(p)\|$ is a continuous application with compact support, let $p_{max}\in\mathbb{R}^3$ be the point where $\|\vec{\nabla}w\|$ reaches its maximum $M:=\|\vec{\nabla}w(p_{max})\|$, M>0. The preceding equation is then equivalent to:

$$\|\vec{u}\| < \frac{1}{M}$$

The non-folding of r can therefore be guaranteed by limiting the amplitude of node displacements. The maximum norm for node displacement is given by the inverse of the maximum gradient norm of the form function under consideration w.

Bijection

Let $V:=V(n)$ be the closed uniting of the cells surrounding the node n. In this part, we will show that if an elementary application r does not fold space then it is also bijective of V in itself but also of R3!R3 since the points outside V are not affected by r.

Implementation

Choice of an Expression of w

To simplify the computing of elastic registration, a polynomial expression of w is chosen. Let π be a third-degree polynomial defined by:

$$\begin{cases}\pi(0)=0\\\pi(1)=1\\\pi'(0)=0\\\pi'(1)=0\end{cases}$$

Its expression is $\pi(t)=t^2(3-2t)$

A form function w defined on the "canonical" cell $[0, 1]^3$ taking value 1 at node $n=(1, 1, 1)^T$ can therefore be obtained as:

$$w(p)=w(p_1,p_2,p_3):=\pi(p_1)\pi(p_2)\pi(p_3)$$

FIG. 6a shows the form function restricted to one dimension i.e. $w=\pi$ over the interval [0,1]. The form function w is defined on the union of neighbouring cells around the node n by a change in variable and scaling to adapt its domain of canonical definition $[0, 1]^3$ to the dimensions of the cells in the discretization mesh of the virtual solid. FIG. 6b shows the changes in variable needed for assembling, from the canonical form function, the form function w over a neighbourhood of 2×2 cells of the map. FIG. 6c shows the tracing of the form function thus obtained $w: \mathbb{R}^2\to\mathbb{R}$.

Non-Folding and Bijection Constraint

The expression of w being chosen, it is possible to compute the amplitude of the maximum allowable node displacement for an elementary registration function r. To define this amplitude, an upper limit M is computed for the quantity $\|\vec{\nabla}w\|$ over the domain $[0,1]^3$.

The derivative of π is $\pi'(t)=6t(1-t)$; it reaches its maximum over [0,1] at $t_{max}=\frac{1}{2}$ where $\pi'(t_{max})=3/2$. This gives the expression of $\vec{\nabla}w$:

$$\vec{\nabla}w(p)=\begin{pmatrix}\pi'(p_1)\pi(p_2)\pi(p_3)\\\pi(p_1)\pi'(p_2)\pi(p_3)\\\pi(p_1)\pi(p_2)\pi'(p_3)\end{pmatrix}$$

On $[0, 1]^3$ we have $$(\pi'(p_1)\pi(p_2)\pi(p_3))^2\leq\left(\frac{3}{2}*1*1\right)^2=\left(\frac{3}{2}\right)^2.$$

This upper limit is valid for each coordinate, therefore $\|\vec{\nabla}w\|\leq\sqrt{3(3/2)^2}$ and hence $\|\vec{\nabla}w\|\leq 3/2\sqrt{3}$.

Given this upper limit for the gradient norm, one sufficient condition which guarantees bijection and thereby non-folding of space for elementary deformation functions defined for a mesh composed of canonical cells [0, 1] is therefore $$\|u\| < 0.38 < \frac{2}{3\sqrt{3}}.$$

This result can be extended to any cell dimension as follows. Let $Cell:=[\alpha, \alpha+L]\times[\beta, \beta+L]\times[\gamma, \gamma+L]$ be a cubic cell of edge L. Let φ be the function $\mathbb{R}^3\to\mathbb{R}^3$ which transforms this cell into a canonical cell $[0, 1]^3$ defined by:

$$\phi(p_1,p_2,p_3):=(\phi_1(p_1),\phi_2(p_2),\phi_3(p_3))=((p_1-\alpha)/L,(p_2-\beta)/L,(p_3-\gamma)/L)$$

The form function w defined on Cell is $$w(p)=w(p_1,p_2,p_3)=\pi(\phi_1(p_2))\pi(\phi_3((p_3))\text{ and:}$$

$$\vec{\nabla}w(p)=\begin{pmatrix}\frac{1}{L}\pi'(\varphi_1(p_1))\pi(\varphi_2(p_2))\pi(\varphi_3(p_3))\\\pi(\varphi_1(p_1))\frac{1}{L}\pi'(\varphi_2(p_2))\pi(\varphi_3(p_3))\\\pi(\varphi_1(p_1))\pi(\varphi_2(p_2))\frac{1}{L}\pi'(\varphi_3(p_3))\end{pmatrix}$$

In the same manner as for the canonical cell, it is possible to conclude that an upper limit for the gradient norm is:

$$\|\vec{\nabla}w\|\leq\frac{3}{2L}\sqrt{3}$$

This leads to the sufficient condition, for a cell of dimension L, guaranteeing bijection and non-folding of the elementary elastic deformation r:

$$\|\vec{u}\| \leq 0.38\,L$$

Since the approach presented here is based on the mechanical modelling of solids, it is chosen to restrict the amplitude of individual displacements of the nodes to the so-called domain of "small deformations". To do so, the amplitudes of the deformations imposed on the cells of the solid are limited to 10% of their dimension, i.e.

$$\|\vec{u}\| \leq 10\%\,L$$

One consequence of this restriction is that the compression and stretching of the space applied to the solid on each iteration are limited. Since $\|\vec{u}\| \leq L/10$ and $\|\vec{\nabla} w(p)\| \leq (3\sqrt{3})/(2\,L)$, then $$1 - \frac{3\sqrt{3}}{20} \leq 1 + \vec{\nabla} w(p) \cdot \vec{u} \leq 1 + \frac{3\sqrt{3}}{20}$$

An approximation $((3\sqrt{3})/20 \cong 0.25980\ldots)$ is given by the above equation of the lower and upper limits of the Jacobian of r valid for all cell dimensions:

$$\forall p \in \text{Cell}, 0.74 < |J_r(p)| < 1.26$$

Energy Minimization

Two sets S and D are considered having the cardinals nS=Card(S) and nD=Card(D). Minimization of the registration energy $E_{reg}$ requires computing of the minimum distance between each point of S and set D. The complexity of the naïve calculation, considering for each point of S its distance to each point of D, is s is nS×nD. Numerous techniques have been proposed to accelerate computing of the closest distance between two sets of points, mainly for rigid registration based on the principle of Iterative Closest Point—ICP.

To accelerate the computing of $E_{reg}$ at each iteration, a Euclidian distance map is computed from the points of D. The distance map is calculated on a 3D mesh discretizing the space around D. At each apex of the mesh gi, the minimum distance to D, d(gi,D) is memorized. This data structure is initialized during the pre-operative phase just after segmentation of the vascular tree D in the MRA images.

The content of the distance map is then saved in the form of a binary file to be read at the start of the surgical procedure by the system before any computing of elastic registration. For a given source point s, the value of d(s,D) is computed by trilinear interpolation among the 8 values read in the mesh of the distance map, associated with the apexes which surround s, {gi}i=s1, . . . , s8. During registration, at each iteration, the best displacement for each node of the mesh, which discretizes the virtual solid, is computed by means of the gradient of $E_{reg}$.

The computing of nodal displacement is performed in two steps:
1. The gradient of $E_{reg}$ relative to node displacements is estimated by finite differences;
2. A search along the direction of steepest descent is performed to estimate the optimal pitch;
3. The amplitude of displacement thus obtained is limited so as to meet a constraint.

Since only the displacements of one node are considered at one time, n, only the three coordinates of the nodal displacement vector $\vec{u}$ are involved in computing of minimization. The minimized function is $f: \mathbb{R}^3 \to \mathbb{R}$ defined by:

$$f(\vec{u}) = E_{reg}(r \circ R)$$

where $r: p \to p + w(o)\vec{u}$ is the elementary registration function associated with the node n, and R is the global registration function assembled before the current iteration.

The strategy consisting of returning to the initial form of the virtual solid, after each iteration, allows the assumption that all the source points at the start of the iteration have already been transformed by R following the above-described algorithm. This enables us to leave aside the history of registration formed by R.

Let $\{s^i\}_{i \in I} \subset S$ be the set of source points whose position belongs to the support of the form function W associated with the mesh node n. Since these are the only points concerned by the displacement of n at the current registration iteration, the computing of registration energy can be restricted to this set. This allows us to express the function to be minimized f as:

$$f(\vec{u}) = E_{reg}(r) = \sum_{i \in I} d(r(s^i), D)$$

Function f is not systematically differentiable relative to $\vec{u}$ due to the square root carried by the distance, and to the operator min(x,y) which operates on the distances between the point clouds. The direction of steepest descent must therefore be estimated locally by centred finite differences. This gives:

$$\forall k = 1, 2, 3, \quad \frac{\partial f}{\partial u_k}(\vec{0}) \approx \frac{f(\epsilon \vec{e_k}) - f(-\epsilon \vec{e_k})}{2\epsilon}$$

where $\epsilon$ is a very small value compared with the maximum amplitude of the possible displacement of n, which is less than 10% of the size of cell L, hence $\epsilon \ll L/10$. As for the vectors $\{\vec{e_k}\}_{k=1,2,3}$, these form the canonical base of $\mathbb{R}^3$.

The vector of steepest descent on f can be written:

$$-\vec{\nabla} f = -\left(\frac{\partial f}{\partial u_1}(\vec{0}), \frac{\partial f}{\partial u_2}(\vec{0}), \frac{\partial f}{\partial u_3}(\vec{0})\right)^T$$

The length of the maximum pitch allowed by the non-folding constraint is 10% of L, which allows the maximum displacement vector of node n in the direction of descent on f to be defined as:

$$\vec{u}_{max} = -\frac{L}{10} \frac{\vec{\nabla} f}{\|\vec{\nabla} f\|}$$

The best nodal displacement with regard to minimization of registration energy therefore corresponds to the minimum of the function $f(\vec{0} + t\vec{u}_{max}) = f(t\vec{u}_{max})$ for $t \in [0, 1]$.

A suitable estimation of this minimum is obtained by approximating the function $f(\vec{0} + t\vec{u}_{max}) = f(t\vec{u}_{max})$ over interval [0,1] by a parabola $P: t \to At^2 + Bt + C$.

The three coefficients of the parabola A, B and C are determined by local information on the behaviour of f and an evaluation of its value at the maximum pitch: $f(\vec{u}_{max})$. Therefore:

$$\begin{cases} P(0) = C = f(\vec{0}) \\ P'(0) = B = \vec{\nabla} f \cdot \vec{u}_{max} = -L/10\|\vec{\nabla} f\| \\ P(1) = A + B + C = f(\vec{u}_{max}) \Rightarrow A = f(\vec{u}_{max}) + L/10\|\vec{\nabla} f\| - f(\vec{0}) \end{cases}$$

Two situations then become possible. If A>0 then P is a convex parabola and its minimum is reached in tmin=−B (2A). In this case, if tmin>1 then the value of the pitch is limited to 1. If on the contrary A<0 then P is a concave parabola and its minimum is reached in tmin=1.

Figure 7:
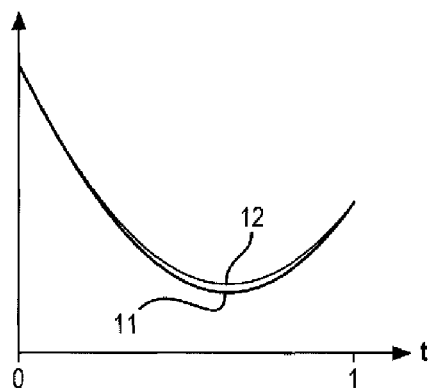
FIG. 7 illustrates an exemplary approximation of a registration energy curve by a parabola.

FIG. 7 shows a representative approximation example of the registration energy curve 11 by a parabola P 12 over the interval [0,1]. Measurements of differences between the two curves performed on a large number of datasets during the course of the registration procedure show the qualities of this approximation. The lower curve 11 is obtained by sampling registration energy over the interval [0,1], the upper curve 12 is the tracing of the parabola P. Despite a slight difference between the values of the two curves, it is noted that the values of t at which these curves reach their maximum are practically identical.

For a given refining level of the discretization of the virtual solid, energy minimization is therefore conducted step by step until no significant reduction can be obtained by applying a displacement to one of the mesh nodes. In this case, if the maximum refining level has not been reached, the mesh is refined and the same procedure is repeated.

Inversion

The computing of the inverse of the elastic registration function $R^{-1}$ will now be described. This computing requires the successive inversion of all the elementary registration functions: $(r^j_{\ j})^{-1}$. Since no analytical expression can be given for $(r^j_{\ j})^{-1}$, the computing of $(r^j_{\ j})^{-1}(q)$ is performed individually for each point q under consideration. To simplify writing, the indices i and j will not be specified hereunder, and an elementary function r will more generally be considered associated with the displacement $\vec{u}$ of the node n.

For a given point q ∈ V(n) its antecedent p=r−1(q) is computed as follows. It was previously seen that p can be written as $p=q+t_p \vec{u}$ where tp is th root of the polynomial function f over the interval [ta, tb]. In fact, since 0≤w(p)≤1 the search interval can be restricted to [max{−1, ta}, 0].

The choice of the expression of the form function $w(p_1, p_2, p_3)=\pi(p_2)\pi(p_3)$ leads to the following expression of f:

$$f: t \rightarrow t+\pi(q_1+tu_1)\pi(q_2+tu_2)\pi(q_3+tu_3)$$

π is a third degree polynomial at t, hence f is of $9^{th}$ degree. There is no explicit formula allowing the roots of a ninth-degree polynomial to be found, therefore recourse must be made to an iterative technique of Newtonian type.

Assuming that the value of ta is already initialized at max{−1, ta}, first the following solution is estimated:

$$t_p^0 := t_a - \frac{f(t_a)}{f(0)-f(t_a)}(0-t_a)$$

Iterations are then carried out as is conventional:

$$t_p^{i+1} = t_p^i - \frac{f(t_p^i)}{f'(t_p^i)}$$

The approximation of $r^{-1}(q)$ at each iteration is given by $p^i := q+t_p^i \vec{u}$ and the corresponding error in deformed space is $\|r(p^i)-q\|=|f(t_p^i)|\|\vec{u}\|$.

The accuracy of the approximation of the inverse is measured in the initial non-deformed space, by evaluating the quantity $\|p^i-p\|$, p is unknown which makes the evaluation of this error difficult. The evaluation of $\|p^i-p\|$ is based on the fact that the invention application $r^{-1}$ is k-Lipschitzian, in other words:

$$\exists k>0, \forall p,q \in \mathbb{R}^3, \|r^{-1}(p)-r^{-1}(q)\| \leq k\|p-q\|$$

With this property it is then possible to increase the error $\|p^i-p\|$ by:

$$\|p^i-p\|=\|r^{-1}(r(p^i))-r^{-1}(q)\| \leq k\|r(p^i)-q\|=k|f(t_p^i)|\|\vec{u}\|$$

It is desired to continue the iterations of the Newtonian algorithm until the desired accuracy is reached i.e. when $\|p^i-p\|<\epsilon$. In the light of the above, this end condition is verified when $|f(t_p^i)|<\epsilon/(k\|\vec{u}\|)$. This inequality forms a reliable end criterion defined in the non-deformed space.

Let us now consider the case of a registration function R composed of several elementary functions rj. In this case, the accuracy of computing of the inverse $R^{-1}$ must be controlled at each inversion step $r_j^{-1}$ of an elementary function. Let us see how we can evaluate the accuracy of the computing of R−1 using the Lipschitz constants of the functions $r_j^{-1}$.

For better clarity, it is assumed that $$R = r_3 \circ r_2 \circ r_1.$$

It is desired to evaluate $R^{-1}=r_1^{-1} \circ r_2^{-1} \circ r_3^{-1}$ having a Lipschitz constant kj for each $r_j^{-1}$.

Figure 8:
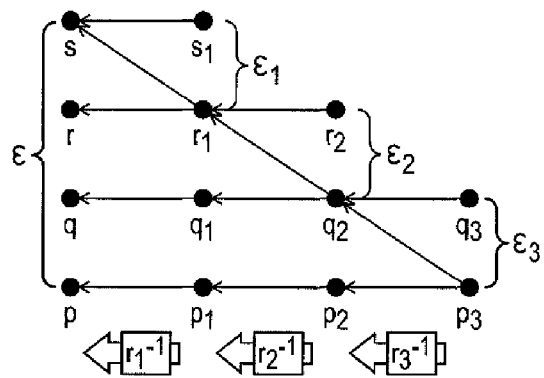
FIG. 8 illustrates three steps of the approximation of the inverse registration function.

Let P∈ $\mathbb{R}^3$ be the sought antecedent of p3=R(p) having as intermediate images p1=r1(p) and p2=r2(r1(p))=r2(p1). FIG. 8, from right to left, illustrates the three steps of the approximation of $R^{-1}(p_3)$ and the successive accumulation of the errors committed at each step:

1. q2 approximates $p_2=r_3^{-1}(p_3)$. The error in the deformed space is $\epsilon_3:=\|q3-p3\|$.

This error is propagated towards the non-deformed space as $\epsilon_3 k_3$, $\epsilon_3$, $k_3 k_2$ and finally $\|q-p\| \leq \epsilon_3 k_3 k_2 k_1$.

2. r1 approximates $q_1=r_2^{-1}(q_2)$ with an error in the deformed space of $\epsilon_2:=\|r_2-q_2\|$;

This error propagates leftwards i.e. towards the non-deformed space as $\epsilon_2 k_2$ then $\|r-q\| \leq \epsilon_2 k_2 k_1$.

3. Finally, s approximates $r=r_1^{-1}(r_1)$ with an error in the deformed space of $\epsilon_1:=\|s_1-r_1\|$ T This error propagates as $\|s-r\| \leq \epsilon_1 k_1$.

The final error can therefore be increased by the sum of the propagated errors:

$$\epsilon = \|s-p\| \leq \|s-r\|+\|r-q\|+\|q-p\| \leq \epsilon_1 k_1+\epsilon_2 k_2 k_1+\epsilon_3 k_3 k_2 k_1$$

The above expression can be immediately extended to any elastic registration function R. If R is composed of N elementary functions and the desired accuracy in the non-deformed space is ϵ, then the approximation effort must be distributed among the N elementary functions by adjusting the accuracy threshold of the Newtonian inversion to:

$$\forall j=1,\ldots,N\epsilon_j = \frac{\epsilon}{N\sum_{i=1}^{j}k_i}$$

where each Lipschitz constant ki must be evaluated only once since it only depends on the amplitude of the displacement applied to the node associated with the elementary function ri, and on the size of the cell at the refining level under consideration.

Filtering of Elastic Registration and Computing of the Displacement Field

As described above, the intra-operative images are noisy and elastic registration may occasionally produce registration artefacts. It is therefore important to set up a strategy allowing the number of erroneous associations to be reduced between source points and target points, each of these associations subsequently translating as a displacement, and there is a risk that their effect will propagate as far as the computing of the biomechanical deformation of the model, the consequence being substantial loss of accuracy.

A robust, simple technique was therefore implemented to eliminate coarse registration errors due to the presence of false vessels in the data derived from segmentation. This method is divided into two phases: direct filtering which is based on computing of the registration function R, followed by inverse filtering which involves the registration inverse: $R^{-1}$.

The role of filtering is to eliminate the associations of points which do not verify a given accuracy criterion. Let dmax be the maximum acceptable distance between a source point and its counterpart in D. Direct filtering allows elimination of the points in S which do not meet the condition $d(R(s),D)<dmax$. The filtered set of source points is $S^f$ defined by:

$$S^f := \{s \in S | d(R(s),D) < d_{max}\}$$

Figure 9:
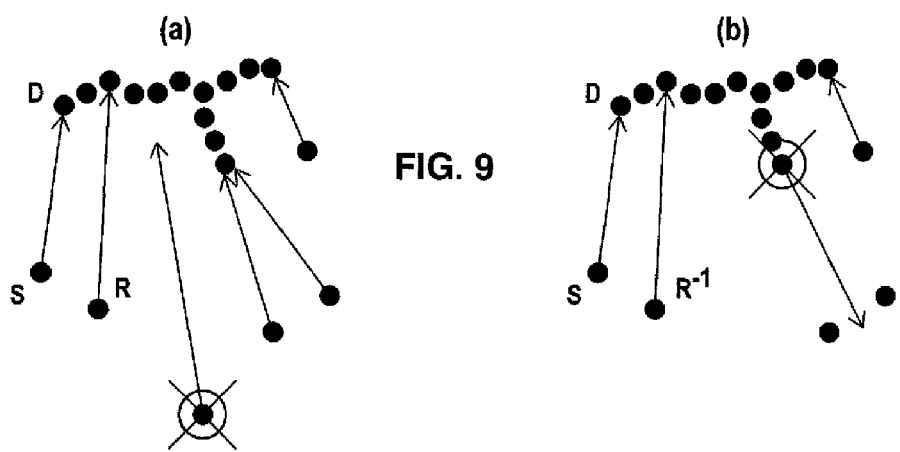
FIG. 9 illustrates direct and indirect filtering steps.

FIG. 9a illustrates the direct filtering step. As can be ascertained in this figure, the source points which have not reached D are eliminated.

The objective of registration procedure is to generate a displacement field corresponding to displacement of the vascular tree structure (in the presentation given here, but more generally of the deformed organic tissue) defined from pre-operative images by D, and which map it to the current configuration S obtained by analysis of intra-operative US Doppler images. With inverse filtering it is possible to verify that the displacement field obtained by inversion of the registration function R effectively transforms points D to S. So as not to take into account the previously eliminated source points, the set S is restricted to $S^f$ and the filtered set of target points $D^b$ is defined as:

$$D^b := \{d \in D | d(R^{-1}(d), S^f) < d_{max}\}$$

FIG. 9b illustrates the inverse filtering step. As illustrated in this figure, the displacements of D which do not reach S are eliminated.

Finally, all the displacements of the vascular tree, from its reference configuration to its current configuration, are assembled using this latter set of points as basis. The displacement field intended for the biomechanical model is therefore given by:

$$Disp := \{u = \overrightarrow{ab}, a \in D^b, b = R^{-1}(a)\}$$

The elastic registration described in detail above allows the construction of an association between two observations of the cerebral vascular tree, pre- and intra-operative, which are of very different type. Computing is guided by minimization of the registration energy which quantifies the similarity between the two structures. Since optimal registration is reached with zero energy, the objective of the registration algorithm is iteratively to minimize the value thereof by causing the current so-called "source" structure to move towards the reference so-called "target" structure.

The rapidity of computing is obtained by means of the prior computing of a distance map on which evaluation of registration and determination of the direction of steepest descent are based, computed on each iteration of the minimization process. The mathematical properties of the registration function family generated by the above-described method guarantee heed of essential physical criteria such as the non-folding of space, non-overlapping of matter and continuity of shift propagation. This elastic registration also has the advantage of being invertible with the desired degree of accuracy.

On the basis of this latter characteristic, post-processing of the result produced by registration is proposed. With this post-processing it is possible to eliminate aberrations due to the presence of noise in intra-operative imaging data. All the finally chosen vascular tree displacements form the input data to the biomechanical model whose role is to extend the scope thereof to the entire volume of the patient's brain in order to simulate the effect of brain-shift.

Figure 2:
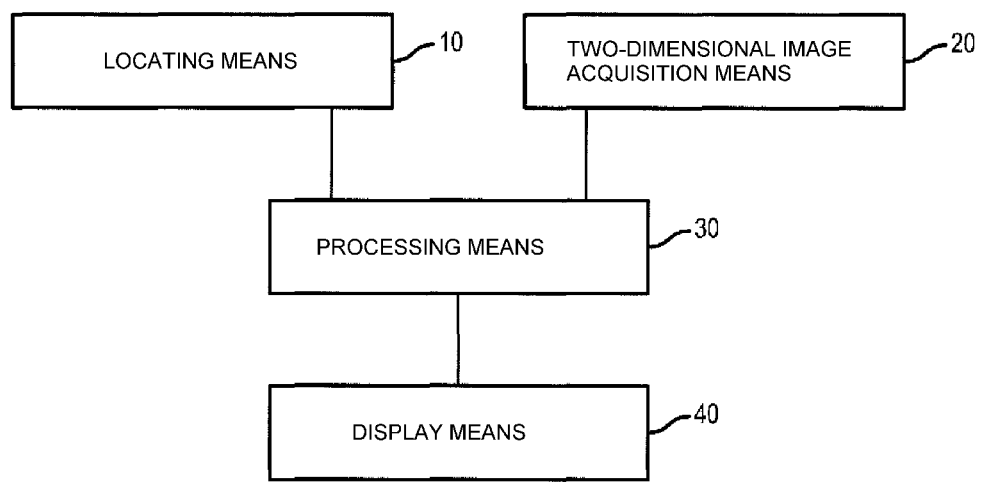
FIG. 2 illustrates one embodiment of the system for implementing the method of the invention.

FIG. 2 illustrates one embodiment of the system for implementing the above-described method. The system comprises locating means 10, acquisition means 20, processing means 30 and display means 40.

The locating means allow the locating in space of the instruments used by the user during the surgical procedure. These locating means may for example comprise a stereoscopic camera and markers associated with the different objects to be located. The locating means 10 also allow the locating in space of the patient's head during the procedure, in particular for spatial repositioning of the reference vascular tree computed from the magnetic resonance angiogram.

The acquisition means 20 allow the acquisition of two-dimensional images during the operation. These acquisition means 20 comprise an ultrasound probe for example which can be located by the locating means 10. The display means for example allow the display of updated pre-operative data. These display means may comprise a monitor.

The processing means allow the implementation of the different computing steps of the method, and in particular:

the processing step 100 of the three-dimensional image of the patient's brain, acquired before surgical procedure, to obtain a reference cerebral arterial tree of the patient, the processing step 200 of the two-dimensional images of the patient's brain acquired during the operation, to reconstitute at least in part the patient's current cerebral arterial tree, the determination step 300, from matching of the reference and current cerebral arterial trees, to determine the deformation field of the vascular tree representing the displacement of the current vascular tree relative to the reference vascular tree, and the application 400 of the determined deformation field of the vascular tree to a biomechanical model of the patient's brain, to estimate the patient's brain-shift.

These processing means may be a computer and may comprise control means to control the different component parts of the system.

Persons skilled in the art will appreciate that numerous modifications can be made to the described method without materially departing from the novel teachings given herein. In particular the registration method described in the foregoing in connection with registration of the cerebral vascular tree can be used to allow the registration of any type of organic tissue which has undergone deformation. Also, although this registration step was presented in connection with sets of source points S and target points D having different numbers of points, the registration step can be applied to sets of data S and D comprising the same number of points. Therefore, the examples given above are evidently particular illustrations only which are in no way limiting.

The invention claimed is:

1. A method for registering a set of source points (S) in a reference image representing an organic tissue with a set of target points (D) in a current image representing a deformed organic tissue, the method comprising determining a registration function (R) by iterative minimization of a registration energy $E_{reg}$, the registration function corresponding to a transformation allowing source points (S) of the reference image to be mapped to corresponding target points (D) in the current image, wherein the registration function (R) is an elastic registration function meeting conditions to guarantee heed of physical criteria of the organic tissue, the conditions comprising:
   (a) a Jacobian of the elastic registration function is greater than 0;
   (b) the registration function is continuously differentiable; and
   (c) the registration function is bijective.

2. The method according to claim 1, wherein the set of source points is of a different type than the set of target points.

3. The method of claim 1, wherein the registration energy $E_{reg}$ of the registration function (R) meets the following equation:

$$E_{reg} = \sum_{s \in S} d(R(s), D)$$

where:
   (s) is a point in the set of source points (S);
   R(s) is a transform of point by the registration function R; and
   d(R(s),D) is a Euclidian distance between the transform of point (s) by the registration function and the set of target points (D).

4. The method of claim 1 further comprising a direct filtering step wherein each point s of the set of source points (S), whose association with a point d in the set of target points (D) verifies a rejection criterion, is deleted so as to obtain a filtered set of source points (S').

5. The method of claim 4, wherein the rejection criterion is a distance between:
   a transform of point (s) in the set of source points (S) by the registration function; and
   a corresponding point (d) in the set of target points (D), is greater than a pre-determined maximum value.

6. The method of claim 4 further comprising an inverse filtering step wherein each point d of the set of target points (D), whose association with a point (s) in the set of source points (S) verifies another rejection criterion, is deleted so as to obtain a filtered set of target points (D').

7. The method of claim 6, wherein the other rejection criterion is that a distance between:
   an inverse transform of point d of the set of target points (D) by an inverse registration function; and
   a corresponding point (s') in the filtered set of source points (S'),
is greater than a pre-determined maximum value.

8. A system for registering a set of source points in a reference image representing an organic tissue with a set of target points in a current image representing the deformed organic tissue, the system comprising a computer for implementing the method of claim 1.

9. A non-transitory computer-readable medium comprising program code instructions for implementing the method of claim 1.

* * * * *